(12) United States Patent
Burckhardt

(10) Patent No.: US 8,389,772 B2
(45) Date of Patent: Mar. 5, 2013

(54) ALDEHYDES CONTAINING HYDROXL GROUPS

(75) Inventor: Urs Burckhardt, Zurich (CH)

(73) Assignee: Sika Technology AG, Baar (CH)

( * ) Notice: Subject to any disclaimer, the term of this patent is extended or adjusted under 35 U.S.C. 154(b) by 269 days.

(21) Appl. No.: 12/671,837

(22) PCT Filed: Aug. 29, 2008

(86) PCT No.: PCT/EP2008/061398
§ 371 (c)(1),
(2), (4) Date: Feb. 2, 2010

(87) PCT Pub. No.: WO2009/027510
PCT Pub. Date: Mar. 5, 2009

(65) Prior Publication Data
US 2011/0195242 A1    Aug. 11, 2011

(30) Foreign Application Priority Data
Aug. 31, 2007  (EP) ..................................... 07115439

(51) Int. Cl.
*C07C 223/00* (2006.01)
*C07C 229/00* (2006.01)
(52) U.S. Cl. ........ 564/502; 564/471; 544/399; 428/221; 428/423.1; 524/591; 525/452; 525/453; 156/331.7
(58) Field of Classification Search .................. 544/399; 564/471, 502; 428/221, 423.1; 524/591; 525/452, 453; 156/331.7
See application file for complete search history.

(56) References Cited

U.S. PATENT DOCUMENTS

| | | |
|---|---|---|
| 1,824,676 A | 9/1931 | Mannich |
| 3,698,898 A | 10/1972 | Grasshoff et al. |
| 4,224,417 A | 9/1980 | Hajek et al. |
| 2006/0122352 A1 | 6/2006 | Burckhardt |

FOREIGN PATENT DOCUMENTS

| | | |
|---|---|---|
| EP | 0 046 288 A1 | 2/1982 |
| EP | 0 254 177 A2 | 1/1988 |
| EP | 1 524 282 A1 | 4/2005 |
| EP | 1 717 253 A1 | 11/2006 |
| GB | 1 193 347 | 5/1970 |
| RU | 2 291 162 C2 | 1/2007 |
| WO | WO 2004/013088 A1 | 2/2004 |
| WO | WO 2005/017005 A1 | 2/2005 |
| WO | WO 2006/074051 A2 | 7/2006 |

OTHER PUBLICATIONS

Johnson, P. et al., "The Chemistry of Hindered Systems. 2. The Acyloin Reaction—an Approach to Regiospecifically Hydroxylated Tetramethylazacycloheptane Systems," J. Org. Chem., 1976, pp. 1768-1773, vol. 41—No. 10.
Mannich, C. et al., "A Synthesis of N-Substituted .alpha. -amino Aldehydes Ueber Eine Sythese von N-Substituierten Beta-Amino-Aldehyden," Berichte Der Deutschen Chemiscen Gesellschaft Abteilung B: Abhandlungen, 1932, pp. 378-385, vol. 65B.
Johnson, P. et al., "The Chemistry of Hindered Systems. Syntheses and Properties of Tetramethylazacycloheptanes and Related Acyclic Amines," J. Org. Chem., 1975, pp. 2710-2720, vol. 40—No. 19.
International Search Report issued in International Application No. PCT/EP2008/061398; Mailed Oct. 29, 2008.
May 14, 2010 International Preliminary Report on Patentability issued in PCT/EP2008/061398.
Johnson et al., "The Chemistry of Hindered Systems.#2. The Acyloin Reaction—an Approach to Regiospecifically Hydroxylated Tetramethylazacycloheptane Systems," *Journal of Organic Chemistry*, vol. 41 (10), 1976, pp. 1768-1773.
Chemical encyclopedia, v. 1, editorship "Soviet encyclopedia," 1988, p. 534, col. 1043 "sealants," (with translation).
Chemical encyclopedia, v. 1, editorship "Great Russian Encyclopedia," 1995, p. 362, cols. 715-716 "adhesion," (with translation).
Mar. 1, 2012 Office Action issued in Russian Patent Application No. 2010112402/04(017353) (with translation).

*Primary Examiner* — Shailendra Kumar
(74) *Attorney, Agent, or Firm* — Oliff & Berridge, PLC

(57) ABSTRACT

The present invention relates to aldehydes of the formula (I) which contain tertiary amino groups and at least one hydroxyl group. Aldehydes of this kind can be utilized broadly. Aldehydes of particular advantage can be incorporated into a polymer, and find use as curing agents and/or catalysts. Preferably they find use in adhesives and sealants.

29 Claims, No Drawings

ALDEHYDES CONTAINING HYDROXL GROUPS

This application is a 371 of PCT/EP2008/061398, filed Aug. 29, 2008.

TECHNICAL FIELD

The invention relates to the field of the aldehydes and to the field of polyurethanes.

STATE OF THE ART

The α-aminoalkylation of aldehydes with formaldehyde and primary or secondary aliphatic amines is disclosed by C. Mannich, for example in U.S. Pat. No. 1,824,676. The β-aminoaldehydes obtainable in this way are also referred to as "Mannich bases". Being versatile synthesis units, they have found wide use.

For certain applications, it would be advantageous to have available aldehydes with further functional groups. Especially in polyurethane chemistry, there is a need for aldehydes which have functional groups reactive toward isocyanate groups and hence can be incorporated covalently into a polyurethane polymer.

SUMMARY OF THE INVENTION

It is therefore an object of the present invention to provide novel aldehydes which have reactive functional groups available for further reactions.

It has been found that, surprisingly, aldehydes according to Claim 1 achieve this object. These are Mannich bases having hydroxyl groups, which have not been described to date. They are usually room temperature liquid compounds which have barely any odour and are preparable from readily available base materials in a simple process. They have tertiary amino groups of relatively low basicity and can act catalytically in chemical reaction systems. Their hydroxyl groups are available for further reactions, for example with isocyanate groups.

These aldehydes are suitable, for example, for preparing aldimines which can be used as hardeners for curable compositions having groups reactive towards amines, such as epoxy groups, anhydride groups or especially isocyanate groups. In compositions having isocyanate groups, the aldehydes released again from the aldimines in the course of curing are incorporated covalently into the polyurethane polymer which forms via the hydroxyl groups thereof and thus remain completely in the composition.

The invention further provides aldehydes according to Claim 9, which are reaction products of the aldehydes described.

The invention further provides curable compositions comprising the aldehydes described, according to Claim 17.

Finally, a process for preparing the aldehydes according to Claim 10 and 11, a cured composition according to Claim 24, uses according to Claim 15, and an article according to Claim 29 constitute further subjects of the present invention.

Further aspects of the invention are the subject of further independent claims. Particularly preferred embodiments of the invention are the subject of the dependent claims.

WAYS OF PERFORMING THE INVENTION

The invention provides aldehydes ALD of the formula (I)

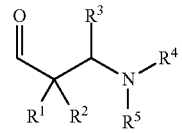

(I)

where
$R^1$ and $R^2$ are either
  each independently a monovalent hydrocarbon radical having 1 to 12 carbon atoms
  or together are a divalent hydrocarbon radical having 4 to 12 carbon atoms which is part of an optionally substituted carbocyclic ring having 5 to 8, preferably 6, carbon atoms;
and
$R^3$ is a hydrogen atom or an alkyl group or an arylalkyl group or an alkoxycarbonyl group, especially having 1 to 12 carbon atoms;
$R^4$ and $R^5$ are either
  each independently a methyl group or a monovalent aliphatic, cycloaliphatic or arylaliphatic radical which has 2 to 20 carbon atoms and optionally has hydroxyl groups or aldehyde groups and optionally contains heteroatoms in the form of ether oxygen or tertiary amine nitrogen, with the proviso that $R^4$ has at least one hydroxyl group,
or
  together are a divalent aliphatic radical which has at least one hydroxyl group and 4 to 20 carbon atoms, and is part of an optionally substituted heterocyclic ring having 5 to 8, preferably 6, ring atoms, this ring optionally containing further heteroatoms in the form of ether oxygen or tertiary amine nitrogen and optionally having aldehyde groups.

$R^1$ and $R^2$ are preferably each a methyl group.
$R^3$ is preferably a hydrogen atom.
$R^4$ and $R^5$ are preferably each a 2-hydroxyethyl group or are each a 2-hydroxypropyl group.

In one embodiment, preferred aldehydes ALD of the formula (I) are those in which the $R^4$ and $R^5$ radicals together have at least two hydroxyl groups. These preferred aldehydes ALD of the formula (I) are aldehydes ALD1 of the formula (I')

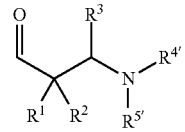

(I')

where
$R^{4'}$ and $R^{5'}$ are either
  each independently a methyl group or a monovalent aliphatic, cycloaliphatic or arylaliphatic radical which has 2 to 20 carbon atoms and optionally has hydroxyl groups or aldehyde groups and optionally contains heteroatoms in the form of ether oxygen or tertiary amine nitrogen, with the proviso that $R^{4'}$ has at least one hydroxyl group, and that $R^{4'}$ and $R^{5'}$ together have at least two hydroxyl groups, or together are a divalent aliphatic radical which has at least two hydroxyl groups and 4 to 20 carbon atoms, and is part of an optionally substituted heterocyclic ring having 5 to 8, preferably 6, ring atoms, this ring optionally containing further heteroatoms in the form of ether oxygen or tertiary amine nitrogen and optionally having aldehyde groups;

and $R^1$, $R^2$ and $R^3$ are each as already defined.

In a further embodiment, preferred aldehydes ALD of the formula (I) are those in which the $R^4$ and $R^5$ radicals together have only one hydroxyl group. These preferred aldehydes ALD of the formula (I) are aldehydes ALD2 of the formula (I″)

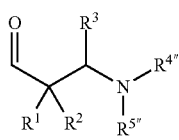
(I″)

where $R^{4″}$ and $R^{5″}$ are either each independently a methyl group or a monovalent aliphatic, cycloaliphatic or arylaliphatic radical which has 2 to 20 carbon atoms and optionally has hydroxyl groups or aldehyde groups, and which optionally contains heteroatoms in the form of ether oxygen or tertiary amine nitrogen, with the proviso that $R^{4″}$ has a hydroxyl group, and that $R^{5″}$ does not have a hydroxyl group;

or together are a divalent aliphatic radical which has a hydroxyl group and 4 to 20 carbon atoms, and is part of an optionally substituted heterocyclic ring having 5 to 8, preferably 6, ring atoms, this ring optionally containing further heteroatoms in the form of ether oxygen or tertiary amine nitrogen and optionally having aldehyde groups;

and $R^1$, $R^2$ and $R^3$ are each as already defined.

Particular preference is given to the aldehydes ALD1 of the formula (I′) which have at least two hydroxyl groups.

Aldehydes ALD1 of the formula (I′) having two hydroxyl groups are most preferred. These most preferred aldehydes ALD1 of the formula (I′) contain, in one embodiment, one $R^{4′}$ radical with two hydroxyl groups and one $R^{5′}$ radical with no hydroxyl group; or, in a further embodiment, one $R^{4′}$ radical with one hydroxyl group and one $R^{5′}$ radical with one hydroxyl group.

Aldehydes ALD of the formula (I) are obtainable especially as the product of a Mannich reaction or of an α-aminoalkylation analogous to the Mannich reaction, as known from the technical literature; they may therefore also be referred to as Mannich bases.

In one embodiment, an aldehyde Y1 of the formula (II), an aldehyde Y2 of the formula (III) and a secondary aliphatic amine C which has at least one hydroxyl group and is of the formula (IV) are converted with elimination of water to an aldehyde ALD of the formula (I).

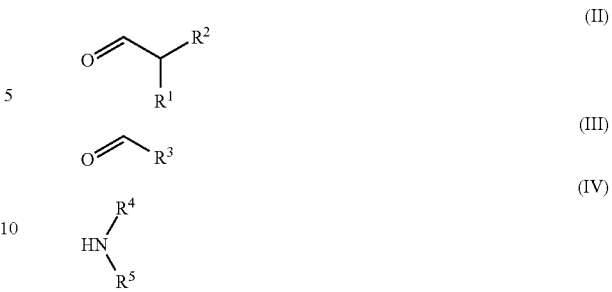

This reaction can either be conducted with the free reagents Y1, Y2 and C of the formulae (II), (III) and (IV), or the reagents can be used partly or completely in derivatized form. The aldehyde Y1 can thus be used as the enolate, as the enol ether, especially as the silyl end ether, or as the enamine. The aldehyde Y2 can be used, for example, in the form of an oligomer—in the case of formaldehyde especially as 1,3,5-trioxane or as paraformaldehyde—or as the hydrate, hemiacetal, acetal, N,O-acetal, aminal or hemiaminal. The secondary aliphatic amine C, finally, can be used, for example, as the salt, especially as the amine hydrochloride or as the amine hydrosulphate, or as the silylamine. It is possible to use a portion of the reagents in free form and a portion in derivatized form, or to proceed only from derivatized forms. In the case of use of reagents in derivatized form, the aldehyde ALD is under some circumstances likewise obtained in derivatized form, for example as the salt; in this case, it can be converted by suitable workup to the free form of the formula (IV). According to the circumstances, it may be advisable additionally to use assistants such as Lewis acids or catalysts in such conversion reactions.

In addition, the reaction can be conducted as a one-pot reaction in which all three reagents can react simultaneously with one another; or else a stepwise method can be selected, by first reacting two of the reagents with one another and then reacting the intermediate thus obtained with the third reagent, it being possible to isolate the intermediate or not. Suitable intermediates of this kind are especially iminium salts, which are obtained from the reaction of an aldehyde Y2, in free or derivatized form, with a salt of a secondary aliphatic amine C, and which can be reacted with an aldehyde Y1, in free or derivatized form, to give the corresponding salt of an aldehyde ALD of the formula (I). Such a stepwise method may have the advantage of enabling milder reaction conditions and hence of providing a higher product yield.

In addition, the reaction can be performed using solvents, especially polar solvents such as water or alcohols, or the reaction can be effected without use of solvents.

In a preferred embodiment, the reaction is conducted as a one-pot reaction with all reagents in free form and the aldehyde ALD is purified by distillation on completion of reaction. Preference is given to using no organic solvents.

Examples of suitable aldehydes Y1 of the formula (II) are the following aldehydes: isobutyraldehyde, 2-methylbutyraldehyde, 2-ethylbutyraldehyde, 2-methylvaleraldehyde, 2-ethylcapronaldehyde, cyclopentanecarboxaldehyde, cyclohexanecarboxaldehyde, 1,2,3,6-tetrahydrobenzaldehyde, 2-methyl-3-phenylpropionaldehyde, 2-phenylpropionaldehyde and diphenylacetaldehyde. Preference is given to isobutyraldehyde.

Examples of suitable aldehydes Y2 of the formula (III) are the following aldehydes: formaldehyde, acetaldehyde, propionaldehyde, butyraldehyde, isobutyraldehyde, phenylacetaldehyde, benzaldehyde and substituted benzaldehydes, and also glyoxylic esters, especially ethyl glyoxylate. Preference is given to formaldehyde.

In one embodiment, suitable amines C of the formula (IV) are secondary aliphatic amines C1 which have at least two hydroxyl groups "Primary amine", "secondary amine" and "tertiary amine" in the present document denote compounds which bear primary, secondary and tertiary amino groups, respectively. The term "primary amino group" denotes an amino group in the form of an $NH_2$ group which is bonded to an organic radical. The term "secondary amino group" denotes an amino group in which the nitrogen atom is bonded to two organic radicals which may also together be part of a ring. The term "tertiary amino group" denotes an amino group in which the nitrogen atom (=tertiary amine nitrogen) is bonded to three organic radicals, where two of these radicals may also together be part of a ring.

"Aliphatic" in the present document refers to an amine or an amino group in which the nitrogen atom is bonded exclusively to aliphatic, cycloaliphatic or arylaliphatic radicals.

Suitable amines C1 having two hydroxyl groups are especially selected from the group consisting of diethanolamine, dipropanolamine, diisopropanolamine, 3-(2-hydroxyethylamino)-1-propanol and 3-(2-hydroxypropylamino)-1-propanol, N-methyl-2,3-dihydroxypropylamine, 3,4-dihydroxypyrrolidine, 2,5-bis(hydroxymethyl)pyrrolidine, 2,6-bis(hydroxymethyl)piperidine, 3,4- or 3,5-dihydroxypiperidine, 2-(2,3-dihydroxypropyl)pyrrolidine and 2-(2,3-dihydroxypropyl)piperidine, and the reaction products of ammonia with two molecules which each have an epoxy group, especially a glycidyl ether group.

Suitable amines C1 having more than two hydroxyl groups are, for example, as follows: 2-(2,3-dihydroxypropylamino) ethanol, 3,4,5-trihydroxy-piperidine, N,N-bis(2,3-dihydroxypropyl)amine, 2,5-bis(2,3-dihydroxypropyl)-pyrrolidine and 2,6-bis(2,3-dihydroxypropyl)piperidine.

The use of amines C1 in the preparation of aldehydes ALD leads especially to the preferred aldehydes ALD1 of the formula (I').

In a further embodiment, suitable amines C of the formula (IV) are secondary amines C2 which have only one hydroxyl group and are selected from the group consisting of alkoxylates of primary amines, such as 2-(N-methylamino)ethanol, 2-(N-ethylamino)ethanol, 2-(N-propylamino)ethanol, 2-(N-isopropylamino)ethanol, 2-(N-butylamino)ethanol, 2-(N-cyclohexylamino)ethanol, 3-(N-methylamino)-2-propanol, 3-(N-ethylamino)-2-propanol, 3-(N-propylamino)-2-propanol, 3-(N-isopropylamino)-2-propanol, 3-(N-butylamino)-2-propanol, 3-(N-cyclohexylamino)-2-propanol, 2-(N-ethylamino-ethoxy)ethanol, and cycloaliphatic hydroxylamines such as 2-pyrrolidine-methanol, 3-hydroxypyrrolidine, 2-piperidinomethanol, 3- or 4-hydroxypiperdine and 1-(2-hydroxyethyl)piperazine.

The use of amines C2 in the preparation of the aldehydes ALD leads especially to the preferred aldehydes ALD2 of the formula (I").

Suitable amines C of the formula (IV) are additionally amines C3 with two secondary aliphatic amino groups and at least one hydroxy group, for example 2-hydroxymethylpiperazine, 2-(2,3-dihydroxypropyl)piperazine, 2,3- or 2,6-bis(hydroxymethyl)piperazine and N,N'-dimethylpropylene-2-oldiamine. The amines C3 are reacted with double the amount of each of aldehyde Y1 and aldehyde Y2. This forms aldehydes ALD in the form of aldehydes which have hydroxyl groups and are of the formula (V),

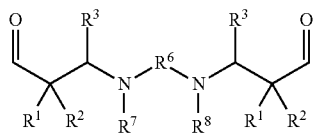

where
$R^6$ is a divalent aliphatic, cycloaliphatic or arylaliphatic radical which has 2 to 20 carbon atoms and optionally has hydroxyl groups, and which optionally contains heteroatoms in the form of ether oxygen or tertiary amine nitrogen;
$R^7$ and $R^8$ are either
  each independently a methyl group or a monovalent aliphatic, cycloaliphatic or arylaliphatic radical which has 2 to 20 carbon atoms and optionally has hydroxyl groups, and which optionally contains heteroatoms in the form of ether oxygen or tertiary amine nitrogen;
or
  together are a divalent aliphatic radical which has at least one hydroxyl group and 4 to 20 carbon atoms, which, together with N—$R^6$—N, forms a heterocyclic ring having 5 to 8, preferably 6, ring atoms, this ring optionally containing further heteroatoms in the form of ether oxygen or tertiary amine nitrogen,
with the proviso that at least one of the $R^6$, $R^7$ and $R^8$ radicals has at least one hydroxyl group,
and $R^1$, $R^2$ and $R^3$ are each as already defined.

In a further embodiment, aldehydes ALD of the formula (I) can also be prepared via primary aliphatic amines C' which have at least one hydroxyl group and are of the formula (IV'), by reacting them with an aldehyde Y1 and an aldehyde Y2 in a molar ratio of 1:2:2 with elimination of water. This forms aldehydes ALD in the form of aldehydes of the formula (VI).

$$H_2N—R^4 \quad (IV')$$

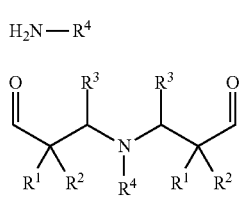

Suitable amines C' of the formula (IV') are primary aliphatic amines having one or more hydroxyl groups, especially those which are selected from the group consisting of aminoalkoxylates such as 2-aminoethanol, 3-amino-1-propanol, 1-amino-2-propanol, 2-amino-1-butanol, 3-(2-hydroxyethoxy)propylamine, 2-(2-aminoethoxy)ethanol, and also 4-(2-aminoethyl)-2-hydroxyethyl-benzene and 3-aminomethyl-3,5,5-trimethylcyclohexanol.

Preferred aldehydes ALD1 are 3-(N-bis(2-hydroxyethyl)amino)-2,2-dimethylpropanal and 3-(N-bis(2-hydroxy-2-methylethyl)amino)-2,2-dimethyl-propanal.

Preferred aldehydes ALD2 are 2,2-dimethyl-3-(N-(2-hydroxyethyl)-methylamino)propanal, 2,2-dimethyl-3-(N-(2-hydroxypropyl)methyl-amino)propanal, 2,2-dimethyl-3-(N-(2-hydroxypropyl)ethylamino)propanal, 2,2-dimethyl-3-(N-(2-hydroxypropyl)isopropylamino)-propanal, 2,2-dimethyl-3-(N-2-hyroxypropyl)butylamino)propanal, 2,2-dimethyl-3-(N-(2-hydroxypropyl)cyclo-hexylamino)propanal and 2,2-dimethyl-3-(N-(N'-(2-hydroxyethyl)piper-azino))propanal.

The aldehydes ALD of the formula (I) can be prepared in the manner described from readily available raw materials in a simple process. They have a series of special properties. For instance, they possess a good thermal stability because the carbon atom in the α position to the aldehyde group does not bear a hydrogen atom, and the elimination of a secondary amine to form an alkene is therefore impossible. They also have a surprisingly good stability with respect to oxidation by atmospheric oxygen. Moreover, the basicity thereof is surprisingly significantly lower than expected for aliphatic amines of similar structure; the pK$_a$ measured for the conjugated acid of an aldehyde ALD is about 2 units lower than that of the conjugated acid of the primary or secondary amine C used to prepare this aldehyde ALD. These surprising properties are possibly connected to an intramolecular 1,4 interaction between amine group and aldehyde group (orbital overlap between the free electron pair of the nitrogen and the π or π* orbital of the carbonyl), as postulated by P. Y. Johnson et al. (J. Org. Chem., vol. 40, no. 19, 1975; pages 2710-2720) on the basis of NMR and UV spectroscopy studies on β-aminoaldehydes.

Finally, the aldehydes ALD, even in the case of relatively low molecular weight, have only a slight odour, if any. This property of low odour intensity, which is surprising for aldehydes, results firstly from the fact that the aldehydes ALD are not very volatile owing to the OH groups present. Moreover, the low odour is probably promoted by the intramolecular 1,4 interaction mentioned and by the steric hindrance of the aldehyde group which is on a tertiary carbon atom.

The aldehydes ALD of the formula (I) can be used very widely.

They can be used as catalysts for chemical reaction systems, for example in curable compositions having isocyanate groups, especially in order to shorten the curing time thereof.

The aldehyde groups and the hydroxyl groups thereof enable further reactions to form further-functionalized reaction products of the aldehydes ALD. They can be reacted, for example, with compounds reactive toward hydroxyl groups to give reaction products having aldehyde groups. Suitable compounds reactive toward hydroxyl groups are, for example, isocyanates, epoxides, anhydrides and carboxylic acids. For example, compounds having isocyanate groups can be converted by the reaction with hydroxyl groups of the aldehydes ALD to give compounds having aldehyde groups, for example polyurethane polymers having aldehyde groups or polyisocyanates having aldehyde groups.

In addition, the aldehyde groups of the aldehydes ALD can be reacted with compounds which have primary amino groups to give aldimines. Aldimines can be used as protected aldehyde groups and/or protected ("blocked") amino groups. Firstly, hydroxy-functional monoaldimines which can in turn be reacted with compounds reactive toward hydroxyl groups to give further-elaborated reaction products are obtainable in this way. Secondly, hydroxy-functional polyaldimines which can be used, for example, in polyurethane chemistry as hardeners are obtainable in this way. When the polyaldimines are contacted with polyisocyanates in the presence of moisture, the primary amino groups released in a formal sense by hydrolysis of the aldimino groups react with the isocyanate groups to release the aldehydes ALD, while the hydroxyl groups thereof likewise react with isocyanate groups. The aldehydes ALD released are finally incorporated covalently into the polymer which forms in the course of curing, which is very advantageous. As a result of the incorporation of the aldehydes, they do not cause any adverse effects in the composition, for example increased shrinkage, emissions into the ambient air, especially of unpleasant odours, or migration effects such as sweating; they likewise do not have an adverse effect on the mechanical properties of the composition, for example by having a plasticizing effect or reducing the stability of the composition with respect to environmental influences such as heat or UV radiation. As already mentioned, aldehydes ALD1 are preferred, since they bear at least two hydroxyl groups, and are thus incorporated covalently into the polymer which forms as at least difunctional hardeners with chain extension or crosslinking in the course of curing of compositions having isocyanate groups. The relatively low basicity of the aldehydes ALD which has been mentioned is advantageous for such a use since strongly basic tertiary amines can excessively accelerate the direct reaction of the isocyanate groups, especially with water, which can have a disruptive effect in the curing of polyurethanes.

In addition, the aldehydes ALD can be used as starter molecules for polyalkoxylations. In this manner, depending on the number of hydroxyl groups present in the aldehyde ALD used, monools or polyols having aldehyde groups are obtainable. Thus, polyols having at least one aldehyde group are obtainable from the polyalkylation of an aldehyde ALD of the formula (I).

Finally, the aldehydes ALD can be used as a source of cationic compounds, by protonating some or all of the tertiary amino groups to ammonium groups or alkylating some or all to quaternary ammonium groups. By protonating or alkylating aldehydes ALD of the formula (I), aldehydes of the formula (VII) are obtainable,

(VII)

where
R$^9$ is a hydrogen atom or an alkyl, cycloalkyl or arylalkyl radical having 1 to 20 carbon atoms;
and R$^1$, R$^2$, R$^3$, R$^4$ and R$^5$ are each as already defined.

To protonate the aldehydes ALD of the formula (I), it is possible to use any desired Brønsted acids, for example hydrochloric acid, sulphuric acid, phosphoric acid, carboxylic acids such as acetic acid or benzoic acid, and sulphonic acids such as methanesulphonic acid or p-toluenesulphonic acid. To alkylate the aldehydes ALD of the formula (I), it is possible to use known alkylating agents, especially methylating agents, for example methyl iodide, dimethyl sulphate, dimethyl phosphonate, diazomethane, methyl fluorosulphate or trimethyloxonium tetrafluoroborate.

It is clear to the person skilled in the art that a cationic aldehyde of the formula (VII) also includes an anion which balances the positive charge of the aldehyde.

The reaction products mentioned here, proceeding from the aldehydes ALD of the formula (I) described, are merely a small selection of the possible advantageous reaction products therefrom and are in no way intended to restrict the use of the aldehydes ALD.

The invention further provides curable compositions comprising at least one polyisocyanate and at least one aldehyde ALD of the formula (I) or at least one aldehyde of the formula (VII).

The term "polyisocyanate" in the present document encompasses compounds having two or more isocyanate groups, irrespective of whether they are monomeric diisocyanates, oligomeric polyisocyanates or polymers which have isocyanate groups and have a relatively high molecular weight.

Suitable aldehydes ALD of the formula (I) are especially the aldehydes ALD of the formula (I) described in detail above, or the preferred embodiments thereof. Suitable aldehydes of the formula (VII) have already been described above.

Preference is given to curable compositions comprising at least one polyisocyanate and at least one aldehyde ALD of the formula (I').

In one embodiment, the curable composition has one component.

In the present document, a "one-component" composition refers to a curable composition in which all constituents of the composition are stored mixed in the same container, and which is storage-stable over a prolonged period at room temperature, i.e. the performance or use properties thereof change only insignificantly, if at all, as a result of the storage, and which cures through the action of moisture and/or heat after application.

The one-component curable composition comprises at least one polyisocyanate whose isocyanate groups are especially present in the form of blocked isocyanate groups.

A "blocked isocyanate group" in the present document is understood to mean an isocyanate group whose reactivity towards nucleophiles, as a result of the above reaction of a free isocyanate group with a blocking agent known from the prior art, for example a phenol, a ketoxime, a pyrazole, a lactam, or a malonic diester, has been reduced to such a degree that it is storage-stable together with suitable hardeners at room temperature and only begins to react with these hardeners under the action of heat and/or moisture, the blocking agent being released or not being released according to the type.

Suitable polyisocyanates with blocked isocyanate groups are commercially available or can be prepared if required by reaction of polyisocyanates with suitable blocking agents.

The one-component curable composition may be moisture-curing and/or heat-curing.

A "heat-curing composition" in the present document is understood to mean a composition comprising blocked isocyanate groups, in which the blocked isocyanate groups, in the course of heating to a suitable temperature, typically in the range from 120 to 200° C., in special cases even at temperatures from 80° C., are activated to such an extent that crosslinking and hence curing occur with suitable hardeners. This operation is also referred to as baking and is typically effected after the application of the composition.

Typically, the complete curing of the one-component composition described is effected through the action of a combination of moisture and heat.

In a further embodiment, the curable composition has two components.

In the present document, a "two-component" composition is understood to mean a curable composition in which the constituents of the composition are present in two separate components which are stored in separate containers and which are each storage-stable. The two components are referred to as component K1 and as component K2. Only just before or during the application of the composition are the two components mixed with one another, and the mixed composition then cures, the curing under some circumstances proceeding or being completed only through the action of moisture and/or heat.

Particular preference is given to two-component curable compositions consisting of a component K1 and a component K2, which compositions comprise at least one polyisocyanate P and at least one aldehyde ALD1 of the formula (I'). In the course of curing thereof, the aldehyde ALD1, owing to its at least two hydroxyl groups, acts as a hardener for the polyisocyanate P and is incorporated covalently into the polymer which forms with chain extension or crosslinking.

Component K1 of the particularly preferred curable two-component composition comprises at least one polyisocyanate P.

In one embodiment, a suitable polyisocyanate P is a polyisocyanate PI in the form of a monomeric di- or triisocyanate or of an oligomer of a monomeric diisocyanate or of a derivative of a monomeric diisocyanate.

Suitable monomeric di- or triisocyanates are, for example, as follows: 1,4-tetramethylene diisocyanate, 2-methylpentamethylene 1,5-diisocyanate, 1,6-hexamethylene diisocyanate (HDI), 2,2,4- and 2,4,4-trimethyl-1,6-hexamethylene diisocyanate (TMDI), 1,10-decamethylene diisocyanate, 1,12-dodecamethylene diisocyanate, lysine and lysine ester diisocyanate, cyclohexane 1,3- and 1,4-diisocyanate, 1-methyl-2,4- and -2,6-diisocyanatocyclohexane and any mixtures of these isomers (HTDI or $H_6TDI$), 1-isocyanato-3,3,5-trimethyl-5-isocyanatomethylcyclohexane (=isophorone diisocyanate or IPDI), perhydro-2,4'- and -4,4'-diphenylmethane diisocyanate (HMDI or $H_{12}MDI$), 1,4-diisocyanato-2,2,6-trimethylcyclohexane (TMCDI), 1,3- and 1,4-bis(isocyanatomethyl)cyclohexane, m- and p-xylylene diisocyanate (m- and p-XDI), m- and p-tetramethyl-1,3- and -1,4-xylylene diisocyanate (m- and p-TMXDI), bis(1-isocyanato-1-methylethyl)naphthalene, dimer and trimer fatty acid isocyanates such as 3,6-bis(9-isocyanatononyl)-4,5-di(1-heptenyl)cyclohexene(dimeryl diisocyanate), $\alpha,\alpha,\alpha',\alpha',\alpha'',\alpha''$-hexamethyl-1,3,5-mesitylene triisocyanate, 2,4- and 2,6-tolylene diisocyanate and any mixtures of these isomers (TDI), 4,4'-, 2,4'- and 2,2'-diphenylmethane diisocyanate and any mixtures of these isomers (MDI), mixtures of MDI and MDI homologues (polymeric MDI or PMDI), 1,3- and 1,4-phenylene diisocyanate, 2,3,5,6-tetramethyl-1,4-diisocyanatobenzene, naphthalene 1,5-diisocyanate (NDI), 3,3'-dimethyl-4,4'-diisocyanatodiphenyl (TODD, dianisidine diisocyanate (DAM), 1,3, 5-tris(isocyanatomethyl)benzene, tris(4-isocyanatophenyl)methane and tris(4-isocyanatophenyl)thiophosphate.

Particularly suitable polyisocyanates PI are oligomers or derivatives of monomeric diisocyanates, especially of HDI, IPDI, TDI and MDI. Commercially available types are especially HDI biurets, for example as Desmodur® N 100 and N 3200 (Bayer), Tolonate® HDB and HDB-LV (Rhodia) and Duranate® 24A-100 (Asahi Kasei); HDI isocyanurates, for example as Desmodur® N 3300, N 3600 and N 3790 BA (all from Bayer), Tolonate® HDT, HDT-LV and HDT-LV2 (Rhodia), Duranate® TPA-100 and THA-100 (Asahi Kasei) and Coronate® HX (Nippon Polyurethane); HDI uretdiones, for example as Desmodur® N 3400 (Bayer); HDI iminooxadiazinediones, for example as Desmodur® XP 2410 (Bayer); HDI allophanates, for example as Desmodur® VP LS 2102 (Bayer); IPDI isocyanurates, for example in solution as Desmodur® Z 4470 (Bayer) or in solid form as Vestanat® T1890/100 (Degussa); TDI oligomers, for example as Desmodur® IL (Bayer); and mixed isocyanurates based on TDI/HDI, for example as Desmodur® HL (Bayer). Additionally particularly suitable are room temperature liquid forms of MDI (known as "modified MDI"), which are mixtures of MDI with MDI derivatives, for example MDI carbodiimides or MDI uretonimines or MDI urethanes, known for example under trade names such as Desmodur® CD, Desmodur® PF, Desmodur® PC (all from Bayer), and mixtures of MDI and MDI homologues (polymeric MDI or PMDI), obtainable under trade names such as Desmodur® VL, Desmodur® VL50, Desmodur® VL R10, Desmodur® VL R20 and Desmodur® VKS 20F (all from Bayer), Isonate® M 309, Voranate® M 229 and Voranate® M 580 (all from Dow) or Lupranat® M 10 R (from BASF).

The aforementioned oligomeric polyisocyanates PI are in practice typically mixtures of substances with different degrees of oligomerization and/or chemical structures. They preferably have a mean NCO functionality of 2.1 to 4.0 and contain especially isocyanurate, iminooxadiazinedione, uretdione, urethane, biuret, allophanate, carbodiimide, uretonimine or oxadiazinetrione groups. These oligomers preferably have a low content of monomeric diisocyanates.

Preferred polyisocyanates PI are room temperature liquid forms of MDI, and the oligomers of HDI, IPDI and TDI, especially the isocyanurates.

In a further embodiment, a suitable polyisocyanate P is a polyurethane polymer PUP having isocyanate groups.

In the present document, the term "polymer" firstly embraces a collective of macromolecules which are chemically homogeneous but different in relation to degree of polymerization, molar mass and chain length, which has been prepared by a poly reaction (polymerization, polyaddition, polycondensation). The term secondly also embraces derivatives of such a collective of macromolecules from poly reactions, i.e. compounds which have been obtained by reactions, for example additions or substitutions, of functional groups on given macromolecules, and which may be chemically homogeneous or chemically inhomogeneous. The term further also comprises what are known as prepolymers, i.e. reactive oligomeric preliminary adducts whose functional groups are involved in the formation of macromolecules.

The term "polyurethane polymer" embraces all polymers prepared by what is known as the diisocyanate polyaddition process. This also includes those polymers which are virtually or entirely free of urethane groups. Examples of polyurethane polymers are polyetherpolyurethanes, polyesterpolyurethanes, polyetherpolyureas, polyureas, polyesterpolyureas, polyisocyanurates and polycarbodiimides.

A suitable polyurethane polymer PUP having isocyanate groups is obtainable by the reaction of at least one polyol with at least one polyisocyanate.

The polyols used for the preparation of a polyurethane polymer PUP may, for example, be the following polyols or mixtures thereof:

polyetherpolyols, also known as polyoxyalkylenepolyols or oligoetherols, which are polymerization products of ethylene oxide, 1,2-propylene oxide, 1,2- or 2,3-butylene oxide, tetrahydrofuran or mixtures thereof, possibly polymerized with the aid of a starter molecule, for example water, ammonia, 1,2-ethanediol, 1,2- and 1,3-propanediol, neopentyl glycol, diethylene glycol, triethylene glycol, the isomeric dipropylene glycols and tripropylene glycols, the isomeric butanediols, pentanediols, hexanediols, heptanediols, octanediols, nonanediols, decanediols, undecanediols, 1,3- and 1,4-cyclohexanedimethanol, bisphenol A, hydrogenated bisphenol A, 1,1,1-trimethylolethane, 1,1,1-trimethylolpropane, glycerol, aniline, and mixtures of the aforementioned compounds. It is possible to use either polyoxyalkylenepolyols which have a low degree of unsaturation (measured to ASTM D-2849-69 and reported in milliequivalents of unsaturation per gram of polyol (meq/g)), prepared, for example, with the aid of double metal cyanide complex catalysts (DMC catalysts), or polyoxyalkylenepolyols with a higher degree of unsaturation, prepared, for example, with the aid of anionic catalysts such as NaOH, KOH, CsOH or alkali metal alkoxides.

Particularly suitable polyetherpolyols are polyoxyalkylenediols and -triols, especially polyoxyalkylenediols. Particularly suitable polyoxyalkylenedi- and -trials are polyoxyethylenedi- and -trials and polyoxypropylenedi- and -trials.

Particularly suitable polyoxypropylenediols and -triols have a degree of unsaturation lower than 0.02 meq/g and a molecular weight in the range from 1000 to 30 000 g/mol, and also polyoxypropylenediols and -triols with a molecular weight of 400 to 8000 g/mol. In the present document, "molecular weight" or "molar mass" is always understood to mean the molecular weight average $M_n$. Especially suitable are polyoxypropylenediols with a degree of unsaturation less than 0.02 meq/g and a molecular weight in the range from 1000 to 12 000, especially between 1000 and 8000 g/mol. Such polyetherpolyols are sold, for example, under the trade name Acclaim® by Bayer.

Likewise particularly suitable are so-called "EO-endcapped" (ethylene oxide-endcapped) polyoxypropylenediols and -trials. The latter are specific polyoxypropylenepolyoxyethylenepolyols which are obtained, for example, by alkoxylating pure polyoxypropylenepolyols with ethylene oxide on completion of the polypropoxylation, and have primary hydroxyl groups as a result.

Styrene-acrylonitrile- or acrylonitrile-methyl methacrylate-grafted polyetherpolyols.

Polyesterpolyols, also known as oligoesterols, prepared by known processes, especially the polycondensation of hydroxycarboxylic acids or the polycondensation of aliphatic and/or aromatic polycarboxylic acids with di- or polyhydric alcohols.

Especially suitable polyesterpolyols are those prepared from di- to trihydric, especially dihydric, alcohols, for example ethylene glycol, diethylene glycol, propylene glycol, dipropylene glycol, neopentyl glycol, 1,4-butanediol, 1,5-pentanediol, 3-methyl-1,5-hexanediol, 1,6-hexanediol, 1,8-octanediol, 1,10-decanediol, 1,12-dodecanediol, 1,12-hydroxystearyl alcohol, 1,4-cyclohexanedimethanol, dimer fatty acid diol (dimer diol), neopentyl glycol hydroxypivalate, glycerol, 1,1,1-trimethylolpropane or mixtures of the aforementioned alcohols, with organic di- or tricarboxylic acids, especially dicarboxylic acids, or the anhydrides or esters thereof, for example succinic acid, glutaric acid, adipic acid, trimethyladipic acid, suberic acid, azelaic acid, sebacic acid, dodecanedicarboxylic acid, maleic acid, fumaric acid, dimer fatty acid, phthalic acid, phthalic anhydride, isophthalic acid, terephthalic acid, dimethyl terephthalate, hexahydrophthalic acid, trimellitic acid and trimellitic anhydride, or mixtures of the aforementioned acids, and also polyesterpolyols formed from lactones, for example from ε-caprolactone, and starters such as the aforementioned di- or trihydric alcohols.

Particularly suitable polyesterpolyols are polyesterdiols.

Polycarbonatepolyols, as obtainable by reaction, for example, of the abovementioned alcohols—used to form the polyesterpolyols—with dialkyl carbonates such as dimethyl carbonate, diaryl carbonates such as diphenyl carbonate, or phosgene.

Particularly suitable substances are polycarbonatediols.

Likewise suitable as polyols are block copolymers which bear at least two hydroxyl groups and have at least two different blocks with polyether, polyester and/or polycarbonate structure of the type described above.

Polyacrylate- and polymethacrylatepolyols.

Polyhydroxy-functional fats and oils, for example natural fats and oils, especially castor oil; or polyols—known as oleochemical polyols—obtained by chemical modification of natural fats and oils, for example the epoxy polyesters or epoxy polyethers obtained by epoxidation of unsaturated oils and subsequent ring opening with carboxylic acids or alcohols, or polyols obtained by hydroformylation and hydrogenation of unsaturated oils; or polyols obtained from natural fats and oils by degradation processes such as alcoholysis or ozonolysis and subsequent chemical linkage, for example by transesterification or dimerization, of the degradation products or derivatives thereof thus obtained. Suitable degradation products of natural fats and oils are especially fatty acids and fatty alcohols, and also fatty acid esters, especially the methyl esters (FAME), which can be derivatized, for example, by hydroformylation and hydrogenation to hydroxy fatty acid esters.

Polyhydrocarbonpolyols, also known as oligohydrocarbonols, for example polyhydroxy-functional polyolefins, polyisobutylenes, polyisoprenes; polyhydroxy-functional ethylene-propylene, ethylene-butylene or ethylene-propylene-diene copolymers, as produced, for example, by Kraton Polymers, polyhydroxy-functional polymers of dienes, especially of 1,3-butadiene, which can especially also be prepared from anionic polymerization; polyhydroxy-functional copolymers of dienes such as 1,3-butadiene or diene mixtures, and vinyl monomers such as styrene, acrylonitrile, vinyl chloride, vinyl acetate, vinyl alcohol, isobutylene and isoprene, for example polyhydroxy-functional acrylonitrile/butadiene copolymers, which can be prepared, for example, from carboxyl-terminated acrylonitrile/butadiene copolymers (commercially available under the Hycar® CTBN name from Noveon) and epoxides or amino alcohols; and hydrogenated polyhydroxy-functional polymers or copolymers of dienes.

These polyols mentioned preferably have a mean molecular weight of 250-30 000 g/mol, especially of 400-20 000 g/mol, and preferably have a mean OH functionality in the range from 1.6 to 3.

In addition to these polyols mentioned, small amounts of low molecular weight di- or polyhydric alcohols, for example 1,2-ethanediol, 1,2- and 1,3-propanediol, neopentyl glycol, diethylene glycol, triethylene glycol, the isomeric dipropylene glycols and tripropylene glycols, the isomeric butanediols, pentanediols, hexanediols, heptanediols, octanediols, nonanediols, decanediols, undecanediols, 1,3- and 1,4-cyclohexanedimethanol, hydrogenated bisphenol A, dimeric fatty alcohols, for example dimer fatty acid dials, 1,1,1-trimethylolethane, 1,1,1-trimethylolpropane, glycerol, pentaerythritol, low molecular weight alkoxylation products of the aforementioned di- and polyhydric alcohols, and mixtures of the aforementioned alcohols, can be used additionally in the preparation of a polyurethane polymer PUP.

The polyisocyanates used for the preparation of a polyurethane polymer PUP may be aliphatic, cycloaliphatic or aromatic polyisocyanates, especially diisocyanates, for example the monomeric diisocyanates as have already been mentioned as suitable polyisocyanates PI, and also oligomers and polymers of these monomeric diisocyanates, and any desired mixtures of these isocyanates. Preference is given to monomeric diisocyanates, especially MDI, TDI, HDI and IPDI.

A polyurethane polymer PUP is prepared in a known manner directly from the polyisocyanates and the polyols, or by stepwise adduction processes, as also known as chain extension reactions.

In a preferred embodiment, the polyurethane polymer PUP is prepared via a reaction of at least one polyisocyanate and at least one polyol, the isocyanate groups being present in a stoichiometric excess relative to the hydroxyl groups. The ratio between isocyanate and hydroxyl groups is advantageously 1.3 to 10, especially 1.5 to 5.

The reaction is advantageously performed at a temperature at which the polyols and polyisocyanates used and the polyurethane polymer formed are present in liquid form.

The polyurethane polymer PUP has a molecular weight of preferably more than 500 g/mol, especially one between 1000 and 30 000 g/mol.

Moreover, the polyurethane polymer PUP preferably has a mean NCO functionality in the range from 1.8 to 3.

Suitable polyisocyanates P are finally also mixtures comprising a polyurethane polymer PUP and a polyisocyanate PI, especially mixtures comprising an MDI-based polyurethane polymer PUP and monomeric and/or polymeric MDI, and, in addition, mixtures comprising an IPDI-based polyurethane polymer PUP and monomeric and/or oligomeric IPDI.

Component K2 of the particularly preferred curable two-component composition comprises at least one aldehyde ALD1 of the formula (I'). Suitable aldehydes ALD1 for this purpose are the above-described aldehydes ALD1 of the formula (I'), or the preferred embodiments thereof as already described in detail. Aldehydes ALD1 of the formula (I') with $R^{4'}$ and $R^{5'}$ radicals which together have two hydroxyl groups are particularly suitable.

Component K2 optionally comprises further compounds reactive towards isocyanate groups, such as polyols, polyamines, amino alcohols, polythiols or blocked amines.

Suitable polyols in component K2 are the same polyols as have already been mentioned as suitable for preparing a polyurethane polymer PUP, and those low molecular weight di- or polyhydric alcohols as mentioned above as suitable for additional use in the preparation of a polyurethane polymer PUP.

Suitable polyamines in component K2 are commercial aliphatic or aromatic polyamines with primary and/or secondary amino groups, as typically used in two-component polyurethane compositions, for example 1,5-diamino-2-methylpentane (MPMD), 1,3-xylylenediamine (MXDA), N,N'-dibutyl-ethylenediamine, 3,5-diethyl-2,4(6)-diaminotoluene (DETDA), 3,5-dimethylthio-2,4(6)-diaminotoluene (Ethacure® 300, Albemarle), and primary and secondary polyoxyalkylenediamines, as obtainable, for example, under the Jeffamine® trade name (from Huntsman Chemicals).

Suitable amino alcohols in component K2 are compounds which have at least one primary or secondary amino group and at least one hydroxyl group, for example 2-aminoethanol, 2-methylaminoethanol, 1-amino-2-propanol and diethanolamine.

Suitable polythiols in component K2 are, for example, liquid mercapto-terminated polymers known under the Thiokol® brand name, and polyesters of thiocarboxylic acids.

Examples of suitable blocked amines optionally present in component K2 are ketimines, oxazolidines, enamines and aldimines. Particularly suitable blocked amines are polyaldimines which are obtainable from the reaction of polyamines with two or more primary amino groups and aldehydes ALD1 of the formula (I'). Further preferred suitable blocked amines are polyaldimines which are obtainable from the reaction of polyamines with two or more primary amino groups and the products from the esterification of carboxylic acids as described in WO 2004/013088 A1, especially the products from the esterification of lauric acid with 3-hydroxypivalaldehyde.

In one embodiment, component K2 comprises water.

The particularly preferred curable two-component composition optionally comprises further constituents, especially assistants and additives used customarily in polyurethane compositions, for example the following:

plasticizers, for example carboxylic esters such as phthalates, for example dioctyl phthalate, diisononyl phthalate or diisodecyl phthalate, adipates, for example dioctyl adipate, azelates and sebacates, organic phosphoric and sulphonic esters or polybutenes;

nonreactive thermoplastic polymers, for example homo- or copolymers of unsaturated monomers, especially from the group comprising ethylene, propylene, butylene, isobutylene, isoprene, vinyl acetate and alkyl (meth)acrylates, especially polyethylenes (PE), polypropylenes (PP), polyisobutylenes, ethylene-vinyl acetate copolymers (EVA) and atactic poly-α-olefins (APAOs);

solvents;

inorganic and organic fillers, for example ground or precipitated calcium carbonates optionally coated with fatty acids, especially stearates, barite ($BaSO_4$, also known as heavy spar), quartz flours, calcined kaolins, aluminium oxides, aluminium hydroxides, silicas, especially finely divided silicas from pyrolysis processes, carbon blacks, especially industrially produced carbon blacks (referred to hereinafter as "carbon black"), PVC powders or hollow spheres;

fibres, for example of polyethylene;

pigments, for example titanium dioxide or iron oxides;

catalysts which accelerate the hydrolysis of blocked amino groups, especially acids, for example organic carboxylic acids such as benzoic acid, salicylic acid or 2-nitrobenzoic acid, organic carboxylic anhydrides such as phthalic anhydride, hexahydrophthalic anhydride and hexahydromethyl-phthalic anhydride, silyl esters of organic carboxylic acids, organic sulphonic acids such as methanesulphonic acid, p-toluenesulphonic acid or 4-dodecylbenzenesulphonic acid, sulphonic esters, other organic or inorganic acids, or mixtures of the aforementioned acids and acid esters;

catalysts which accelerate the reaction of the isocyanate groups, for example organotin compounds such as dibutyltin diacetate, dibutyltin dilaurate, dibutyltin dichloride, dibutyltin diacetylacetonate and dioctyltin dilaurate, bismuth compounds such as bismuth trioctoate and bismuth tris(neodecanoate), and compounds containing tertiary amino groups, such as 2,2'-dimorpholinodiethyl ether and 1,4-diazabicyclo[2.2.2]octane;

rheology modifiers, for example thickeners or thixotropic agents, for example urea compounds, polyamide waxes, bentonites or fumed silicas;

reactive diluents and crosslinkers, for example monomeric diisocyanates, and also oligomers and derivatives of these polyisocyanates, adducts of monomeric polyisocyanates with short-chain polyols, and also adipic dihydrazide and other dihydrazides, and also polyisocyanates with blocked isocyanate groups, as already mentioned above;

blocked amines, for example in the form of ketimines, oxazolidines, enamines or other aldimines;

desiccants, for example molecular sieves, calcium oxide, high-reactivity isocyanates such as p-tosyl isocyanate, orthoformic esters, tetra-alkoxysilanes such as tetraethoxysilane;

organoalkoxysilanes, also referred to hereinafter as "silanes", for example epoxysilanes, (meth)acryloylsilanes, isocyanatosilanes, vinylsilanes, carbamatosilanes, alkylsilanes, S-(alkylcarbonyl)mercaptosilanes and aldiminosilanes, and oligomeric forms of these silanes;

stabilizers against heat, light and UV radiation;

flame-retardant substances;

surface-active substances, for example wetting agents, levelling agents, devolatilizers or defoamers;

biocides, for example algicides, fungicides or substances which inhibit fungal growth.

When such further constituents are used, it is advantageous to ensure that they do not significantly impair the storage stability of the particular component K1 or K2 of the composition. If such additives are present as a constituent of component K1, it should be ensured that these additives do not trigger the crosslinking of the isocyanate groups to a significant degree during storage. More particularly, this means that additives used in this way should contain at most traces of water, if any. It may be advisable to chemically or physically dry certain additives before they are mixed into component K1.

In the case of component K2, in addition to these, further assistants and additives are additionally possible, which are storable together with free isocyanate groups only briefly, if at all. These are especially further catalysts, especially tertiary amines and metal compounds.

The two components K1 and K2 are prepared separately from one another, for component K1 with the exclusion of moisture. The two components K1 and K2 are storage-stable separately from one another, i.e. they can each be stored in a suitable package or arrangement, for example in a drum, a pouch, a bucket, a cartridge or a bottle, over a period of several months, for example, before use, without their particular properties changing to a degree relevant for the use thereof.

For use of the two-component composition, the two components K1 and K2 are mixed with one another. It should be ensured that the mixing ratio is selected such that the constituents reactive towards isocyanate groups are in a suitable ratio to the isocyanate groups of component K1. More particularly, the ratio is 0.1 to 1.1, preferably 0.5 to 0.95, more preferably 0.6 to 0.9, equivalents of the sum of the hydroxyl groups, amino groups, mercapto groups and protected amino groups present per equivalent of isocyanate groups, protected amino groups in the form of oxazolidino groups being counted double. In the course of curing, excess isocyanate groups react with moisture, especially with air humidity.

The two components K1 and K2 are mixed by a suitable process, for example by means of a static mixer. The mixing can be effected continuously or batchwise. The mixed composition is then applied to a substrate, optionally by means of a suitable application aid. In doing so, it has to be ensured that not too much time passes between the mixing of the components and the application, since excessive preliminary reaction of the constituents of the mixed composition before application can disrupt the function of the cured composition, for example by virtue of the adhesion to the substrate being built up only in an inadequate or retarded manner. The maximum period of time within which the mixed composition should be applied is referred to as "pot life".

After components K1 and K2 have been mixed, curing commences. In the course of this, the groups of component K1 reactive toward isocyanate groups—hydroxyl groups, primary and secondary amino groups and mercapto groups—react with the isocyanate groups. If the composition contains blocked amines, these likewise react with the isocyanate groups, provided that the blocked amino groups thereof come into contact with moisture, for example with moisture from the air. Excess isocyanate groups finally react directly with water, especially with moisture from the air. As a result of these reactions, the composition cures to give a solid material; this process is also referred to as crosslinking.

The curable composition described has a series of advantages.

An aldehyde ALD1 of the formula (I') comprises a tertiary amino group. Such aldehydes can therefore exert a catalytic effect on the reaction of the isocyanate groups and thus accelerate the curing. It is advantageous in this context that its basicity is comparatively low, since strongly basic tertiary amines can disrupt the hydrolysis of any aldimino groups present and/or excessively accelerate the direct reaction of the isocyanate groups, especially with water, which can result in incomplete or uncontrolled curing.

In addition, the aldehyde ALD1 of the formula (I') acts as a hardener for polyisocyanates, since it bears at least two hydroxyl groups on the $R^{4'}$ and $R^{5'}$ radicals together and therefore reacts with the isocyanate groups with chain extension or crosslinking of the polymer which forms and does not lead to chain termination.

As a result of the incorporation of the aldehyde ALD1 into the polymer being cured, the potentially catalytically active tertiary amino groups are also incorporated covalently into the polymer which forms. After the incorporation into the polymer, the catalytic activity of the tertiary amino group is significantly reduced owing to the restricted mobility thereof, which may be advantageous for the durability of the material.

The aldehyde groups are preserved in the course of curing and are likewise incorporated into the cured material. They can, if desired, be used for further reactions.

A further advantage of the compositions described lies in the comparatively low odour of the aldehydes ALD1. As a result, the compositions have hardly any odour before, during and after the curing, which is not necessarily to be expected in the presence of aldehydes.

Preferred applications of the curable compositions described are adhesives, sealants, potting compositions, coatings, floor coverings, paints, coating materials, primers or foams.

A further aspect of the present invention relates to a process for bonding a substrate S1 to a substrate S2, which comprises the steps of
i) applying an above-described curable composition to a substrate S1;
ii) contacting the applied composition with a substrate S2 within the open time of the composition;
or
i') applying an above-described composition to a substrate S1 and to a substrate S2;
ii') contacting the applied compositions with one another within the open time of the composition;
the substrate S2 consisting of the same material as, or a different material than, the substrate S1.

A further aspect of the present invention relates to a process for sealing. This comprises the step of
i'') applying an above-described curable composition between a substrate S1 and a substrate S2, such that the composition is in contact with the substrate S1 and the substrate S2;
the substrate S2 consisting of the same material as, or a different material than, the substrate S1.

Typically, the sealant is injected into a joint.

A further aspect of the present invention relates to a process for coating a substrate S1. This comprises the step of
i''') applying an above-described curable composition to a substrate S1 within the open time of the composition.

In these three processes, suitable substrates S1 and/or S2 are, for example, inorganic substrates such as glass, glass ceramic, concrete, mortar, brick, tile, gypsum and natural stones such as granite or marble; metals or alloys such as aluminium, steel, nonferrous metals, galvanized metals; organic substrates such as leather, fabrics, paper, wood, resin-bound woodbase materials, resin-textile composite materials, plastics such as polyvinyl chloride (rigid and flexible PVC), acrylonitrile-butadiene-styrene copolymers (ABS), SMC (sheet moulding composites), polycarbonate (PC), polyamide (PA), polyesters, PMMA, polyesters, epoxy resins, polyurethanes (PU), polyoxymethylene (POM), polyolefins (PO), especially surface-plasma-, -corona- or -flame-treated polyethylene (PE) or polypropylene (PP), ethylene/propylene copolymers (EPM) and ethylene/propylene-diene terpolymers (EPDM); coated substrates such as powder-coated metals or alloys; and paints and coating materials, especially automotive coating materials.

The substrates can be pretreated if required before the application of the composition. Such pretreatments include especially physical and/or chemical cleaning processes, for example grinding, sandblasting, brushing or the like, or treatment with detergents or solvents, or the application of an adhesion promoter, of an adhesion promoter solution or of a primer.

The curable composition can be applied within a broad temperature spectrum. For example, the composition can be applied at room temperature, but it can also be applied at lower or higher temperatures.

After the application of the compositions described as an adhesive, sealant, potting composition, coating, floor covering, paint, coating material, primer or foam, an article is obtained. This article is especially a built structure, especially a built structure in construction or civil engineering, or an industrial good or a consumer good, especially a window, a domestic appliance, or a mode of transport, especially a water or land vehicle, preferably an automobile, a bus, a truck, a train or a ship, or an installable component of a mode of transport, or an article in the furniture, textile or packaging industry.

EXAMPLES

1. Description of the Measurement Methods

The viscosity was measured on a Physica UM thermostated cone-plate viscometer (cone diameter 20 mm, cone angle 1°, cone tip-plate distance 0.05 mm, shear rate 10 to 1000 $s^{-1}$).

The amine content, i.e. the total content of free amino groups and—if present—blocked amino groups (aldimino groups) in the compounds prepared, was determined by titrimetric means (with 0.1N $HClO_4$ in glacial acetic acid, against crystal violet) and is always reported in mmol N/g.

The $pK_a$ for the conjugated acid of a Mannich base was determined approximately using the half-neutralization potential in the potentiometric titration of approx. 1 mmol of Mannich base in 50 ml of water with 0.1N HCl.

Infrared spectra were measured on a Perkin-Elmer 1600 FT-IR instrument as undiluted films on a horizontal ATR measurement unit with a ZnSe crystal; the absorption bands are reported in wavenumbers ($cm^{-1}$) (measurement window: 4000-650 $cm^{-1}$); the addition sh indicates a band which appears as a shoulder, the addition br a broad band.

GC-MS was carried out under the following conditions: Optima-5-MS column, 30 m×0.25 mm, film thickness 0.5 µm; heating rate 15° C./min from 60° C. to 320° C., then held at 320° C. for 15 min; He carrier gas, 14 psi; split 15 ml/min; $EI^+$ ionization method. For the gas chromatogram, the retention time of the product signal ($t_R$) is reported. In the mass spectrum, only the largest peaks are reported (as m/z); the relative intensity (in %) and, if possible, tentative assignment of the molecular fragment are in brackets.

2. Preparation of Aldehydes

Example 1

Aldehyde ALD-1

3-(N-Bis(2-hydroxyethyl)amino)-2,2-dimethylpropanal

A round-bottom flask under a nitrogen atmosphere was initially charged with 83.4 g (1.00 mol) of 36% aqueous formaldehyde and 75.7 g (1.05 mol) of isobutyraldehyde. With good stirring and ice cooling, 105.1 g (1.00 mol) of diethanolamine were slowly added dropwise from a dropping funnel, while ensuring that the temperature of the reaction mixture did not rise above 20° C. On completion of addition, the mixture was left to stir for one hour at room temperature. The resulting clear, colourless reaction mixture was stirred under reflux in an oil bath at 80° C. over 2 hours and cooled to room temperature, and the volatile constituents were distilled off in a water jet vacuum at 80° C. This gave 181.2 g (96% of theory) of crude product as a clear, yellowish oil, which had an amine content of 5.40 mmol N/g and a viscosity of 23.7 Pa·s at 20° C. The crude product contained, as well as 3-(N-bis(2-hydroxyethyl)amino)-2,2-dimethyl-propanal, smaller proportions of 3-hydroxy-2,2-dimethylpropanal, N-(2-hydroxyethyl)oxazolidine and N-(2-hydroxyethyl)-2-isopropyloxazolidine (according to GC-MS analysis).

$pK_a \approx 7.1$.

IR: 3358br (OH), 2950, 2929sh, 2913, 2870, 2830, 2719sh br (CHO), 1721 (C=O), 1464, 1391, 1359, 1302br, 1206, 1147, 1078sh, 1037, 966, 940, 920, 883, 786.

GC-MS: $t_R$=10.3 min; mass spectrum: 189 (2, [M]$^+$), 172 (3, [M-OH]$^+$), 158 (11, [M-CH$_2$OH]$^+$), 128 (4), 118 (100, [M-C(CH$_3$)$_2$CHO]$^+$), 116 (15), 102 (6), 98 (5), 88 (2, [118-CHOH]$^+$), 88 (72), 86 (21), 74 (50), 56 (51).

Example 2

Aldehyde ALD-2

3-(N-Bis(2-hydroxy-2-methylethyl)amino)-2,2-dimethylpropanal

Under the same conditions as in Example 1, 83.4 g (1.00 mol) of 36% aqueous formaldehyde were reacted with 75.7 g (1.05 mop) of isobutyraldehyde and 133.2 g (1.00 mol) of diisopropanolamine, and worked up. This gave 199.4 g (92% of theory) of crude product as a clear, yellowish oil, which had an amine content of 4,87 mmol N/g and a viscosity of 8.2 Pa·s at 20° C. The crude product contained, as well as 3-(N-bis(2-hydroxy-2-methylethyl)amino)-2,2-dimethylpropanal, smaller proportions of 3-hydroxy-2,2-dimethylpropanal, N-(2-hydroxy-2-methylethyl)oxazolidine and N-(2-hydroxy-2-methylethyl)-2-isopropyloxazolidine (according to GC-MS analysis).

$pK_a \approx 7.1$.

IR: 3392br (OH), 2966, 2933, 2872, 2818, 2719sh br (CHO), 1722 (C=O), 1461, 1409, 1375, 1328, 1274, 1209, 1158, 1130, 1090sh, 1055, 1028sh, 978, 945, 914, 891, 864, 839, 818, 786.

GC-MS: $t_R$=10.3 min; mass spectrum: 217 (3, [M]$^+$), 172 (30, [M-CH(CH$_3$)OH]$^+$), 146 (44, [M-C(CH$_3$)$_2$CHO]$^+$), 144 (21), 130 (6), 126 (6), 116 (7), 114 (10), 102 (100, [146-C(CH$_3$)OH]$^+$), 100 (18), 88 (16), 70 (38).

Example 3

Aldehyde ALD-3

3-(1-(4-(2-hydroxyethyl)piperazino))-2,2-dimethylpropanal

Under the same conditions as described in Example 1, 32.0 g (0.38 mol) of 36% aqueous formaldehyde were reacted with 29.1 g (0.40 mol) of isobutyraldehyde and 50.0 g (0.38 mol) of 1-(2-hydroxyethyDpiperazine, and worked up. This gave 81.4 g (99% of theory) of crude product as a clear, viscous, orange oil which had an amine content of 9.17 mmol N/g.

IR: 3395br (OH), 3170br, 2944, 2869, 2806, 2768sh, 2695 (CHO), 1723 (C=O), 1458, 1402sh, 1374, 1361sh, 1349, 1336, 1318, 1294, 1276, 1153, 1120, 1096, 1085sh, 1052, 1011, 974sh, 942, 913, 877, 834, 815, 771.

3. Use of Aldehydes as Hardeners in Polyurethane Compositions

Examples 4 and 5 and Comparative Examples 6 and 7

2K Potting Compositions

For each example, the particular constituents of component K2 according to table 1 were weighed in the parts by weight specified, without preceding drying, into a screwtop polypropylene beaker, and mixed by means of a centrifugal mixer (SpeedMixer™ DAC 150, FlackTek Inc.; 2 min at 3000 rpm) to give a homogeneous cream. To this were added the parts by weight of PMDI specified in table 1 as component K1, and mixed in (30 sec at 3000 rpm). The ratio between the isocyanate groups of component K1 and the hydroxyl groups of component K2 is always 1.1.

TABLE 1

Composition of the two-component potting compositions.

| | Example | | | |
|---|---|---|---|---|
| | 4 | 5 | 6 (comp.) | 7 (comp.) |
| Component K1: | | | | |
| PMDI[a] | 38.0 | 37.2 | 37.7 | 29.7 |
| Component K2: | | | | |
| castor oil[b] | 22.5 | 22.5 | 22.5 | 22.5 |
| dimer fatty acid diol[c] | 17.5 | 17.5 | 17.5 | 22.5 |
| triol[d] | 4.75 | 4.75 | 4.75 | 4.75 |
| diol[e] | ALD-1, 5.0 | ALD-2, 5.0 | TPG, 5.0 | — |
| acid catalyst[f] | 0.25 | 0.25 | 0.25 | 0.25 |
| molecular sieve[g] | 2.0 | 2.0 | 2.0 | 2.0 |
| chalk[h] | 48.0 | 48.0 | 48.0 | 48.0 |

[a]Desmodur ® VKS 20 F, Bayer; NCO content = 30.0% by wt.
[b]Fluka; OH number = 165 mg KOH/g.
[c]Sovermol ® 908, Cognis; OH number = 200 mg KOH/g.
[d]Desmophen ® 4011 T, Bayer; OH number = 550 mg KOH/g.
[e]the diols used were the aldehydes ALD-1 from Example 1 and ALD-2 from Example 2 and TPG = tripropylene glycol, OH number = 583 mg KOH/g.
[f]Salicylic acid (5% by wt. in dioctyl adipate).
[g]Purmol ® 4ST, CU Chemie Uetikon; pore size 4 Å.
[h]Omyacarb ® 5-GU, Omya.

The potting compositions thus obtained were tested for curing rate and mechanical properties. Indications of the curing rate were obtained firstly by measuring the tack-free time of the potting composition, immediately after the mixing of components K1 and K2. To this end, the mixed composition was applied to paperboard in a layer thickness of approx. 2 mm and the time taken, under standard climatic conditions (23±1° C., 50±5% relative air humidity), when the surface of the coating composition was tapped lightly using an .DPE pipette, for no residues to remain any longer on the pipette for the first time was determined. Secondly, the later curing was monitored by periodically measuring the Shore D hardness to DIN 53505.

To test the mechanical properties, the potting composition was cast as a film with a layer thickness of approx. 2 mm into a planar PTFE mould, and the film was cured under standard climatic conditions for 7 days and tested to DIN EN 53504 for tensile strength, elongation at break and modulus of elasticity (at 0.5-3.0% extension, pulling speed: 10 mm/min).

The results of these tests are listed in table 2.

TABLE 2

Properties of the two-component potting compositions.

| | Example | | | |
|---|---|---|---|---|
| | 4 | 5 | 6 (comp.) | 7 (comp.) |
| Tack-free time (min.)[a] | 34 | 27 | 108 | 48 |
| Shore D after 1 day | 83 | 89 | 71 | 60 |
| Shore D after 3 days | 93 | 94 | 84 | 75 |
| Shore D after 7 days | 95 | 96 | 85 | 82 |
| Shore D after heat treatment[b] | 96 | 96 | 94 | 88 |
| Tensile strength (MPa) | 14.6 | 30.4 | 9.6 | 8.1 |
| Elongation at break (%) | 6 | 3.5 | 30 | 60 |
| Modulus of elasticity (MPa) | 370 | 770 | 175 | 100 |

[a]tack-free time in minutes.
[b]4 h at 105° C., specimen cured for 7 days under standard climatic conditions.

4. Use of Aldehydes for Preparation of Aldimines

Example 8

Dialdimine Proceeding from Aldehyde ALD-1

In a round-bottom flask under a nitrogen atmosphere, 68.2 g of polyetherdiamine(polyoxypropylenediamine with a mean molecular weight of approx. 240 g/mol; Jeffamine® D-230, Huntsman; amine content 8.29 mmol N/g) and 117.6 g of aldehyde ALD-1 from Example 1 were weighed, and the mixture was stirred at room temperature for one hour. Thereafter, the volatile constituents were removed under reduced pressure (10 mbar, 80° C.). Yield: 177.1 g of a clear, yellow oil with an amine content of 6.78 mmol N/g and a viscosity of 9.8 Pa·s at 20° C.

IR: 3391br (OH), 2964, 2926, 2868, 1662 (C=N), 1469, 1456sh, 1392sh, 1373, 1294, 1106sh, 1049, 1004sh, 926, 903, 877.

Example 9

Dialdimine Proceeding from Aldehyde ALD-2

Under the same conditions as described in Example 8, 27.2 g of isophoronediamine (Vestamin® IPD, Degussa; amine content 11.67 mmol N/g) and 71.8 g of aldehyde ALD-2 from Example 2 were reacted. Yield: 93.2 g of a clear, yellow honey with an amine content of 7.66 mmol N/g and a viscosity of 150 Pa·s at 20° C.

IR: 3393br (OH), 2962, 2926, 2898, 2868, 2837, 2818, 1662 (C=N), 1459, 1408, 1373, 1364, 1333, 1273, 1159, 1133, 1116sh, 1058, 1003, 976sh, 945, 909, 891sh, 864, 838.

Example 10

Dialdimine Proceeding from Aldehyde ALD-2

Under the same conditions as described in Example 8, 37.7 g of polyetherdiamine(polyoxypropylenediamine with a mean molecular weight of approx. 240 g/mol; Jeffamine® D-230, Huntsman; amine content 8.29 mmol N/g) and 70.6 g of aldehyde ALD-2 from Example 2 were reacted. Yield: 103.4 g of a clear, yellow-brownish oil with an amine content of 6.26 mmol N/g and a viscosity of 4.0 Pa·s at 20° C.

IR: 3419br (OH), 2965, 2925, 2918, 2868, 2822sh, 1662 (C=N), 1457, 1408sh, 1373, 1331, 1274, 1196sh, 1106, 1089, 1059, 1019, 1002, 977, 944, 910, 865, 838.

Example 11

Monoaldimine Proceeding from Aldehyde ALD-1

Under the same conditions as described in Example 8, 6.55 g of 2-(2-aminoethoxy)ethanol (DGA; Diglycolamine® Agent, Huntsman; amine content 9.39 mmol N/g) and 13.36 g of aldehyde ALD-1 from Example 1 were reacted. Yield: 16.25 g of a clear, yellow oil with an amine content of 7.18 mmol N/g and a viscosity of 3.4 Pa·s at 20° C.

IR: 3358br (OH), 2928, 2865, 2716sh, 1943br, 1663 (C=N), 1467, 1459, 1391, 1358, 1285, 1238, 1123, 1044, 1003sh, 940sh, 924sh, 890, 815, 785, 770.

The invention claimed is:
1. Aldehyde ALD of the formula (I'):

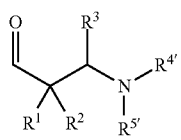

(I')

where
$R^1$ and $R^2$ are either
each independently a monovalent hydrocarbon radical having 1 to 12 carbon atoms
or
together are a divalent hydrocarbon radical having 4 to 12 carbon atoms which is part of an optionally substituted carbocyclic ring having 5 to 8 carbon atoms;
$R^3$ is a hydrogen atom or an alkyl group or an arylalkyl group or an alkoxycarbonyl group; and
$R^{4'}$ and $R^{5'}$ are either
each independently a methyl group or a monovalent aliphatic, cycloaliphatic or arylaliphatic radical which has 2 to 20 carbon atoms and optionally has hydroxyl groups or aldehyde groups and optionally contains heteroatoms in the form of ether oxygen or tertiary amine nitrogen, with the proviso that $R^{4'}$ has at least one hydroxyl group, and that $R^{4'}$ and $R^{5'}$ together have at least two hydroxyl groups,
or
together are a divalent aliphatic radical which has at least two hydroxyl groups and 4 to 20 carbon atoms, and is part of an optionally substituted heterocyclic ring having 5 to 8 ring atoms, this ring optionally containing further heteroatoms in the form of ether oxygen or tertiary amine nitrogen and optionally having aldehyde groups.

2. Aldehyde according to claim 1, wherein $R^1$ and $R^2$ are each a methyl group.

3. Aldehyde according to claim 1, wherein $R^3$ is a hydrogen atom.

4. Aldehyde according to claim 1, wherein $R^{4'}$ and $R^{5'}$ are each a 2-hydroxyethyl group or a 2-hydroxypropyl group.

5. Aldehyde according to claim 1, wherein the aldehyde ALD is an aldehyde ALD2 of the formula (I''):

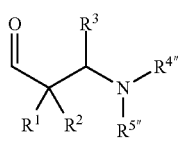

(I'')

where $R^{4''}$ and $R^{5''}$ are either each independently a methyl group or a monovalent aliphatic, cycloaliphatic or arylaliphatic radical which has 2 to 20 carbon atoms and optionally has hydroxyl groups or aldehyde groups, and which optionally contains heteroatoms in the form of ether oxygen or tertiary amine nitrogen, with the proviso that $R^{4''}$ has at least two hydroxyl groups, and that $R^{5''}$ does not have a hydroxyl group;

or together are a divalent aliphatic radical which has a hydroxyl group and 4 to 20 carbon atoms, and is part of an optionally substituted heterocyclic ring having 5 to 8 ring atoms, this ring optionally containing further heteroatoms in the form of ether oxygen or tertiary amine nitrogen and optionally having aldehyde groups.

6. Aldehyde of the formula (V)

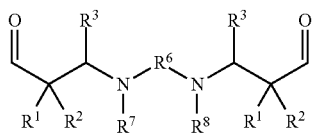

where $R^1$ and $R^2$ are either each independently a monovalent hydrocarbon radical having 1 to 12 carbon atoms or together are a divalent hydrocarbon radical having 4 to 12 carbon atoms which is part of an optionally substituted carbocyclic ring having 5 to 8 carbon atoms;

$R^3$ is a hydrogen atom or an alkyl group or an arylalkyl group or an alkoxycarbonyl group;

$R^6$ is a divalent aliphatic, cycloaliphatic or arylaliphatic radical which has 2 to 20 carbon atoms and optionally has hydroxyl groups, and which optionally contains heteroatoms in the form of ether oxygen or tertiary amine nitrogen;

$R^7$ and $R^8$ are either each independently a methyl group or a monovalent aliphatic, cycloaliphatic or arylaliphatic radical which has 2 to 20 carbon atoms and optionally has hydroxyl groups, and which optionally contains heteroatoms in the form of ether oxygen or tertiary amine nitrogen;

or together are a divalent aliphatic radical which has at least one hydroxyl group and 4 to 20 carbon atoms, which, together with $N-R^6-N$, forms a heterocyclic ring having 5 to 8 ring atoms, this ring optionally containing further heteroatoms in the form of ether oxygen or tertiary amine nitrogen, with the proviso that at least one of the $R^6$, $R^7$ and $R^8$ radicals has at least one hydroxyl group.

7. Aldehyde according to claim 1, wherein the aldehyde ALD is an aldehyde of the formula (VI'):

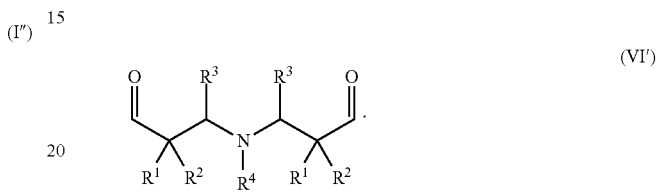

(VI')

8. Aldehyde of the formula (VII')

(VII)

where $R^9$ is a hydrogen atom or an alkyl, cycloalkyl or arylalkyl radical having 1 to 20 carbon atoms, and the aldehyde of the formula (VII) is obtainable by protonation or alkylation from an aldehyde ALD of the formula (I') according to claim 1.

9. Process for preparing an aldehyde according to claim 1, wherein an aldehyde Y1 of the formula (II):

(II)

an aldehyde Y2 of the formula (III):

(III)

and a secondary aliphatic amine C which has at least two hydroxyl groups and is of the formula ('IV):

('IV)

are reacted with elimination of water to give an aldehyde ALD of the formula (I').

10. Process for preparing an aldehyde, wherein at least one primary aliphatic amine C' which has at least one hydroxyl group and is of the formula (IV'):

 (IV')

is reacted with an aldehyde Y1 of the formula (II):

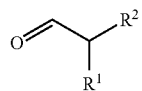 (II)

and an aldehyde Y2 of the formula (III):

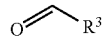 (III)

in a molar ratio of 1:2:2 with elimination of water to give an aldehyde of the formula (VI):

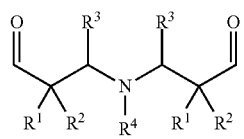 (VI)

where
$R^1$ and $R^2$ are either
each independently a monovalent hydrocarbon radical having 1 to 12 carbon atoms
or
together are a divalent hydrocarbon radical having 4 to 12 carbon atoms which is part of an optionally substituted carbocyclic ring having 5 to 8 carbon atoms;
$R^3$ is a hydrogen atom or an alkyl group or an arylalkyl group or an alkoxycarbonyl group;
$R^4$ is a methyl group or a monovalent aliphatic, cycloaliphatic or arylaliphatic radical which has 2 to 20 carbon atoms and optionally has hydroxyl groups or aldehyde groups and optionally contains heteroatoms in the form of ether oxygen or tertiary amine nitrogen, with the proviso that $R^4$ has at least one hydroxyl group.

11. Process for preparing an aldehyde, wherein an aldehyde Y1 of the formula (II):

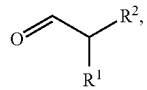 (II)

an aldehyde Y2 of the formula (III):

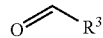 (III)

and a secondary aliphatic amine C which has at least one hydroxyl group and is of the formula (IV):

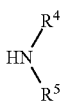 (IV)

are reacted with elimination of water to give an aldehyde ALD of the formula (I):

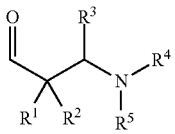 (I)

where
$R^1$ and $R^2$ are either
each independently a monovalent hydrocarbon radical having 1 to 12 carbon atoms
or
together are a divalent hydrocarbon radical having 4 to 12 carbon atoms which is part of an optionally substituted carbocyclic ring having 5 to 8 carbon atoms:
$R^3$ is a hydrogen atom or an alkyl group or an arylalkyl group or an alkoxycarbonyl group:
$R^4$ and $R^5$ are either
each independently a methyl group or a monovalent aliphatic, cycloaliphatic or arylaliphatic radical which has 2 to 20 carbon atoms and optionally has hydroxyl groups or aldehyde groups and optionally contains heteroatoms in the form of ether oxygen or tertiary amine nitrogen, with the proviso that $R^4$ has at least one hydroxyl group,
or
together are a divalent aliphatic radical which has at least one hydroxyl group and 4 to 12 carbon atoms, and is part of an optionally substituted heterocyclic ring having 5 to 8 ring atoms, this ring optionally containing further heteroatoms in the form of ether oxygen or tertiary amine nitrogen, and optionally having aldehyde groups; and the amine C is an amine C1 which has at least two hydroxyl groups, and which is selected from the group consisting of diethanolamine, dipropanolamine, diisopropanolamine, 3-(2-hydroxyethylamino)-1-propanol and 3-(2-hydroxypropylamino)-1-propanol, N-methyl-2,3-dihydroxypropylamine, 3,4-dihydroxypyrrolidine, 2,5-bis(hydroxymethyl)-pyrrolidine, 2,6-bis(hydroxymethyl)piperidine, 3,4- or 3,5-dihydroxy-piperidine, 2-(2,3-dihydroxy-propyl)pyrrolidine and 2-(2,3-dihydroxypropyl)-piperidine, and the reaction products of ammonia with two molecules which each have an epoxy group.

12. Process according to claim 9, wherein the amine C is a secondary amine C2 which has at least two hydroxyl groups and which is selected from the group consisting of alkoxylates of primary amines.

13. Process according to claim 10, wherein the amine C' is selected from the group consisting of aminoalkoxylates, 2-amino-ethanol, 3-amino-1-propanol, 1-amino-2-propanol, 2-amino-1-butanol, 3-(2-hydroxy-ethoxy)propylamine, 2-(2-aminoethoxy)ethanol, 4-(2-aminoethyl)-2-hydroxyethylbenzene, and 3-aminomethyl-3,5,5-trimethylcyclo-hexanol.

14. A method for preparing a composition, the method comprising:
adding an aldehyde ALD of the formula (I') according to claim 1 to a composition based on isocyanates or epoxy resins; wherein the composition is a member selected from the group consisting of adhesives, sealants, potting compositions, coatings, floor coverings, paints, coating materials, primers and foams.

15. Polyol which has at least one aldehyde group and is obtainable from the polyalkoxylation of an aldehyde ALD of the formula (I):

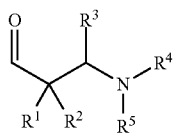

(I)

where
$R^1$ and $R^2$ are either
each independently a monovalent hydrocarbon radical having 1 to 12 carbon atoms
or
together are a divalent hydrocarbon radical having 4 to 12 carbon atoms which is part of an optionally substituted carbocyclic ring having 5 to 8 carbon atoms;
$R^3$ is a hydrogen atom or an alkyl group or an arylalkyl group or an alkoxycarbonyl group:
$R^4$ and $R^5$ are either
each independently a methyl group or a monovalent aliphatic, cycloaliphatic or arylaliphatic radical which has 2 to 20 carbon atoms and optionally has hydroxyl groups or aldehyde groups and optionally contains heteroatoms in the form of ether oxygen or tertiary amine nitrogen, with the proviso that $R^4$ has at least one hydroxyl group,
or
together are a divalent aliphatic radical which has at least one hydroxyl group and 4 to 12 carbon atoms, and is part of an optionally substituted heterocyclic ring having 5 to 8 ring atoms, this rinu optionally containing further heteroatoms in the form of ether oxygen or tertiary amine nitrogen, and optionally having aldehyde groups.

16. Curable composition comprising at least one polyisocyanate and at least one aldehyde ALD of the formula (I):

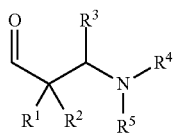

(I)

where
$R^1$ and $R^2$ are either
each independently a monovalent hydrocarbon radical having 1 to 12 carbon atoms
or
together are a divalent hydrocarbon radical having 4 to 12 carbon atoms which is part of an optionally substituted carbocyclic ring having 5 to 8 carbon atoms;
$R^3$ is a hydrogen atom or an alkyl group or an arylalkyl group or an alkoxycarbonyl group:
$R^4$ and $R^5$ are either
each independently a methyl group or a monovalent aliphatic, cycloaliphatic or arylaliphatic radical which has 2 to 20 carbon atoms and optionally has hydroxyl groups or aldehyde groups and optionally contains heteroatoms in the form of ether oxygen or tertiary amine nitrogen, with the proviso that $R^4$ has at least one hydroxyl group,
or
together are a divalent aliphatic radical which has at least one hydroxyl group and 4 to 12 carbon atoms, and is part of an optionally substituted heterocyclic ring having 5 to 8 ring atoms, this ring optionally containing further heteroatoms in the form of ether oxygen or tertiary amine nitrogen, and optionally having aldehyde groups.

17. Curable composition comprising at least one polyisocyanate and at least one aldehyde ALD1 of the formula (I') according to claim 1.

18. Curable composition according to claim 17, wherein it is a one-component composition, and in that it comprises at least one polyisocyanate whose isocyanate groups are present in the form of blocked isocyanate groups.

19. Curable composition according to claim 17, wherein it is a two-component composition consisting of a component K1 and a component K2, which component K1 comprises at least one polyisocyanate P.

20. Curable composition according to claim 19, wherein the polyisocyanate P is a polyisocyanate PI in the form of a monomeric di- or triisocyanate or of an oligomer of a monomeric diisocyanate or of a derivative of a monomeric diisocyanate.

21. Curable composition according to claim 19, wherein the polyisocyanate P is a polyurethane polymer PUP which has isocyanate groups and is obtainable by the reaction of at least one polyol with at least one polyisocyanate.

22. Curable composition according to claim 19, wherein component K2 comprises water.

23. Cured composition obtained by the reaction of a curable composition according to claim 16 and water.

24. Process for bonding a substrate S1 to a substrate S2, which comprises the steps of
i) applying a curable composition according to claim 16 to a substrate S1;
ii) contacting the applied composition with a substrate S2 within the open time of the composition;
or
i') applying a composition according to claim 16 to a substrate S1 and to a substrate S2;
ii') contacting the applied compositions with one another within the open time of the composition;
the substrate S2 consisting of the same material as, or a different material than, the substrate S1.

25. Process for sealing, which comprises the step of
i") applying a curable composition according to claim 16 between a substrate S1 and a substrate S2, such that the composition is in contact with the substrate S1 and the substrate S2;
the substrate S2 consisting of the same material as, or a different material than, the substrate S1.

26. Process for coating a substrate S1, which comprises the step of
i'") applying a curable composition according to claim 16 to a substrate S1 within the open time of the composition.

27. Process according to claim 24, characterized in that the substrate S1 and/or the substrate S2 is an inorganic substrate such as glass, glass ceramic, concrete, mortar, brick, tile, gypsum or natural stone such as granite or marble; a metal or an alloy, such as aluminium, steel, nonferrous metal, galvanized metal; an organic substrate such as wood, a plastic such as PVC, polycarbonate, PMMA, polyethylene, polypropylene, polyester, epoxy resin; a coated substrate such as powder-coated metal or alloy; or a paint or a coating.

28. Article which has been bonded by a process according to claim 24.

29. Article according to claim 28, wherein the article is a built structure, or an industrial good or a consumer good, or a mode of transport, or an installable component on a mode of transport, or an article in the furniture, textile or packaging industry.

* * * * *

UNITED STATES PATENT AND TRADEMARK OFFICE
CERTIFICATE OF CORRECTION

| | | |
|---|---|---|
| PATENT NO. | : 8,389,772 B2 | Page 1 of 1 |
| APPLICATION NO. | : 12/671837 | |
| DATED | : March 5, 2013 | |
| INVENTOR(S) | : Burckhardt | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 371 days.

Signed and Sealed this
Twenty-sixth Day of November, 2013

Margaret A. Focarino
*Commissioner for Patents of the United States Patent and Trademark Office*